(12) United States Patent
Kon et al.

(10) Patent No.: US 11,364,333 B2
(45) Date of Patent: Jun. 21, 2022

(54) BIDIRECTIONAL FLOW CATHETER

(71) Applicants: UNIVERSITY OF MARYLAND, BALTIMORE, Baltimore, MD (US); UNIVERSITY OF MARYLAND MEDICAL SYSTEM, LLC, Baltimore, MD (US)

(72) Inventors: Zachary Kon, Baltimore, MD (US); Mehrdad Ghoreishi, Baltimore, MD (US); Chetan Pasrija, Gaithersburg, MD (US); Bartley Griffith, Gibson Island, MD (US); Gregory Bittle, Baltimore, MD (US)

(73) Assignees: UNIVERSITY OF MARYLAND, BALTIMORE, Baltimore, MD (US); UNIVERSITY OF MARYLAND MEDICAL CENTER, LLC, Baltimore, MD (US)

( * ) Notice: Subject to any disclaimer, the term of this patent is extended or adjusted under 35 U.S.C. 154(b) by 77 days.

(21) Appl. No.: 16/754,382

(22) PCT Filed: Oct. 10, 2018

(86) PCT No.: PCT/US2018/055160
§ 371 (c)(1),
(2) Date: Apr. 8, 2020

(87) PCT Pub. No.: WO2019/075020
PCT Pub. Date: Apr. 18, 2019

(65) Prior Publication Data
US 2020/0306440 A1    Oct. 1, 2020

Related U.S. Application Data

(60) Provisional application No. 62/570,148, filed on Oct. 10, 2017.

(51) Int. Cl.
*A61M 1/36* (2006.01)
*A61M 25/00* (2006.01)

(52) U.S. Cl.
CPC ........ *A61M 1/3659* (2014.02); *A61M 1/3666* (2013.01); *A61M 25/007* (2013.01);
(Continued)

(58) Field of Classification Search
CPC .............. A61M 1/3659; A61M 1/3666; A61M 25/007; A61M 2025/0018; A61M 2025/0073
(Continued)

(56) References Cited

U.S. PATENT DOCUMENTS

| 4,973,321 A | 11/1990 | Michelson |
| 5,171,218 A | 12/1992 | Fonger et al. |

(Continued)

FOREIGN PATENT DOCUMENTS

| EP | 0619745 | 11/1995 |
| WO | 2016/137212 | 9/2016 |

OTHER PUBLICATIONS

International Search Report issued in co-pending application No. PCT/US2018/055160 dated Dec. 27, 2018.
(Continued)

*Primary Examiner* — Phillip A Gray
(74) *Attorney, Agent, or Firm* — Whiteford, Taylor & Preston, LLP; Gregory M. Stone

(57) ABSTRACT

Disclosed herein is a bidirectional intravascular cannula, or catheter, that is configured to provide and return blood in a patient bidirectionally. The bidirectional intravascular cannula is configured to reduce or obviate the need for a second cannula, such as currently available unidirectional cannulae, to be placed in a second or opposite direction of flow. Users would include cardiac surgeons, intensivists, vascular sur-
(Continued)

geons, ER doctors, IR doctors and cardiologist who use peripheral cannulation for ECLS or cardiopulmonary bypass. The cannula allows continued flow to a patient's limb even with the cannula proximally in the vessel. The cannula further allows larger size cannula to be placed without the need for additional distal catheter placement.

16 Claims, 15 Drawing Sheets

(52) U.S. Cl.
CPC .............. *A61M 2025/0018* (2013.01); *A61M 2025/0073* (2013.01)

(58) Field of Classification Search
USPC .......................................................... 604/43
See application file for complete search history.

(56) References Cited

U.S. PATENT DOCUMENTS

| | | |
|---|---|---|
| 5,330,433 A | 7/1994 | Fonger et al. |
| 5,916,193 A | 6/1999 | Stevens et al. |
| 7,393,339 B2 | 7/2008 | Zawacki et al. |
| 8,092,415 B2 | 1/2012 | Moehle et al. |
| 8,795,523 B2 | 8/2014 | Moshinsky et al. |
| 2001/0000528 A1 | 4/2001 | Cho |
| 2005/0182354 A1 | 8/2005 | Quinn |
| 2009/0081079 A1 | 3/2009 | Johns |
| 2009/0240197 A1 | 9/2009 | Cowan et al. |
| 2012/0259273 A1 | 10/2012 | Moshinsky et al. |
| 2013/0085438 A1* | 4/2013 | MacMeans ........... A61M 25/00 604/523 |
| 2014/0330250 A1 | 11/2014 | Moshinsky et al. |
| 2016/0114124 A1 | 4/2016 | Tal |
| 2016/0121079 A1 | 5/2016 | Walther et al. |

OTHER PUBLICATIONS

Extended European Search Report issued in co-pending application No. 18866864.4 dated Jun. 9, 2021.

\* cited by examiner

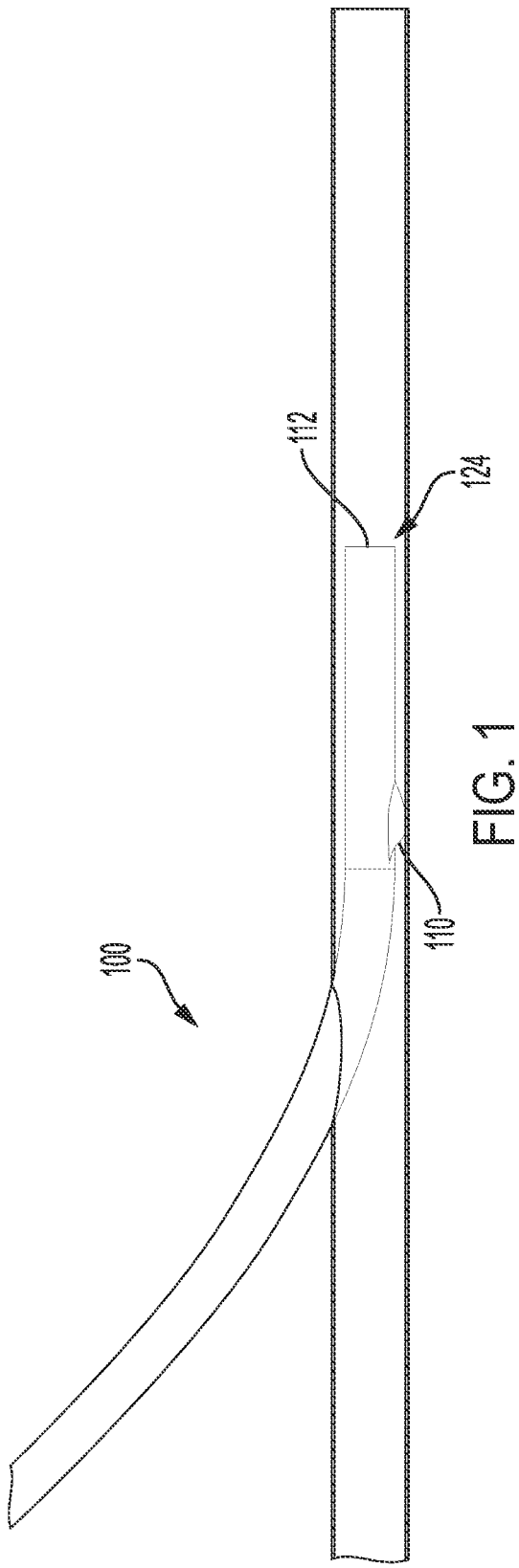
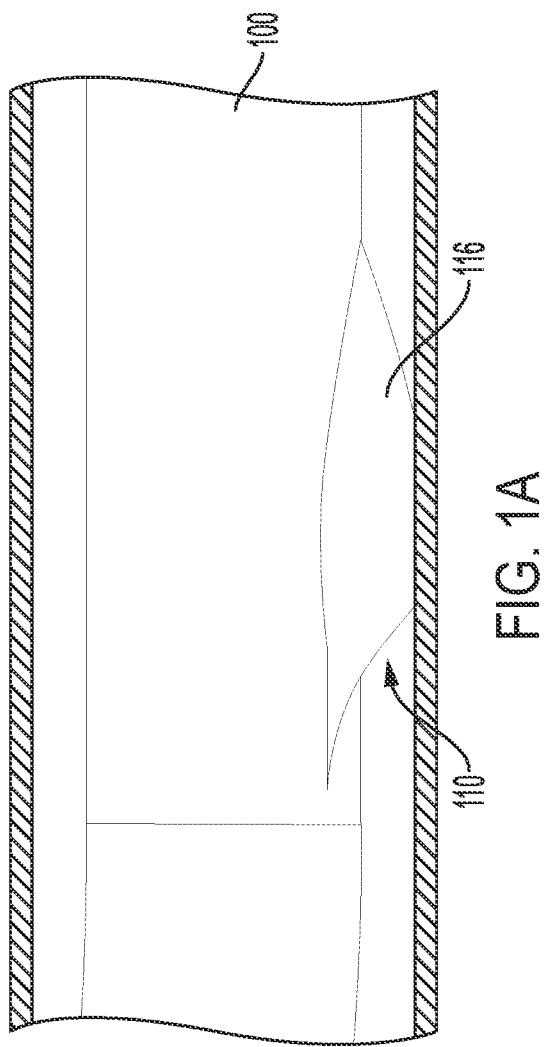

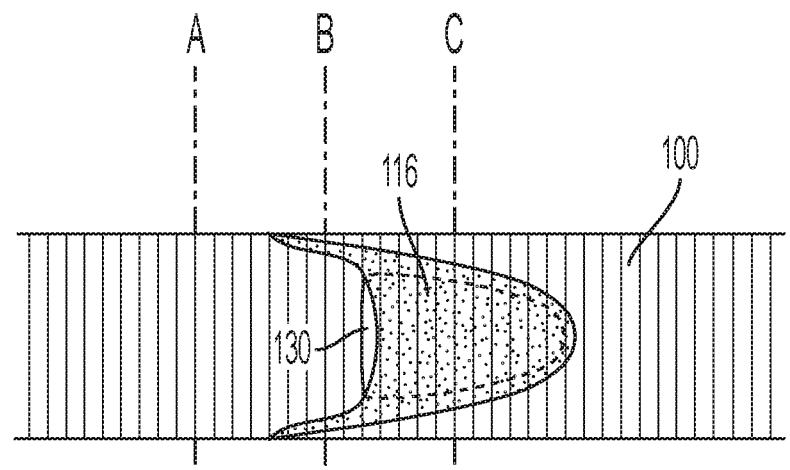
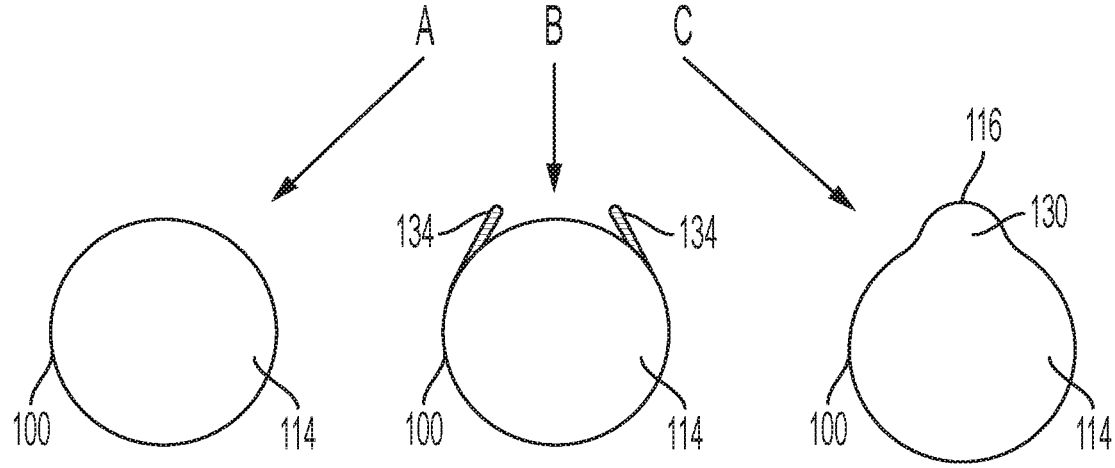
FIG. 6
FIG. 6A   FIG. 6B   FIG. 6C

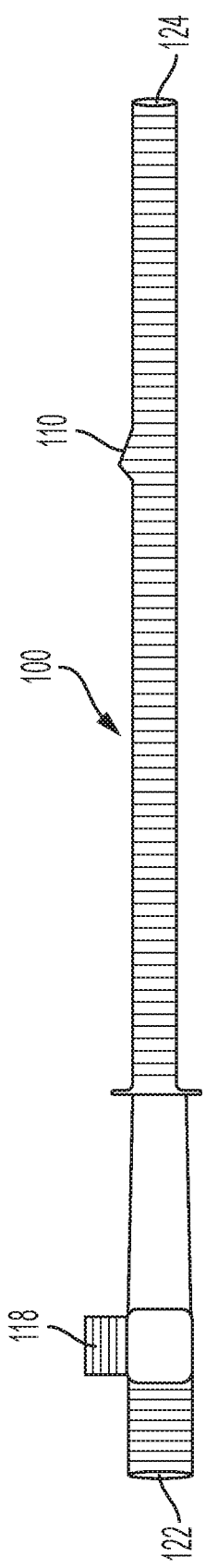
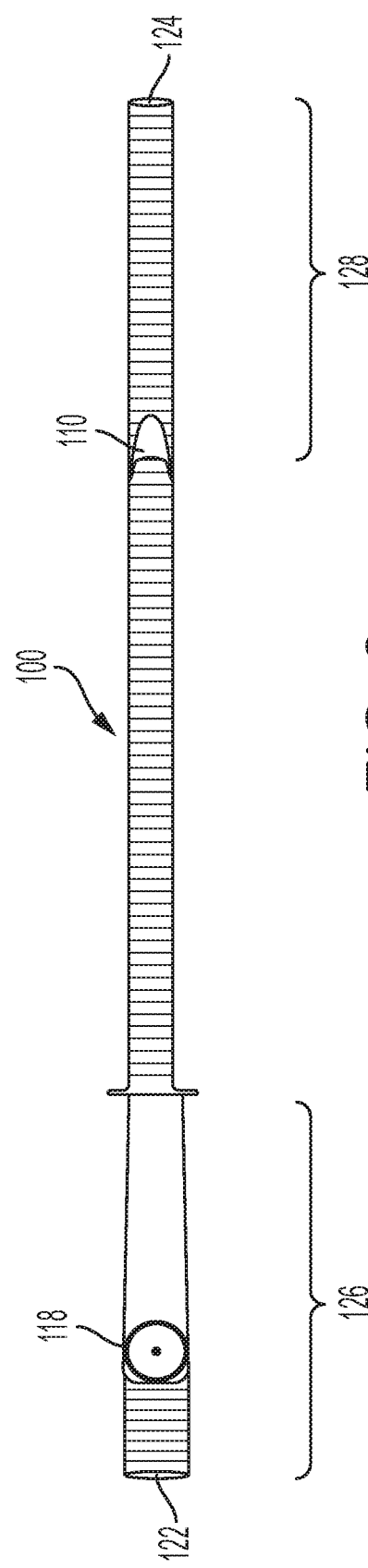

BIDIRECTIONAL FLOW CATHETER

FIELD OF THE INVENTION

The present invention relates generally to the field of medical devices, and more particularly to cannulae and systems using cannulae for peripheral extra corporeal life support (ECLS), including cardiac or pulmonary indication.

BACKGROUND

Blood circulation in a person's heart and lungs is described here to provide a better understanding of certain aspects of embodiments of the invention as set forth herein. Blood travels in a patient's body to a patient's heart from the upper part of the body through the superior vena cava (SVC), and from the lower part of the body through the inferior vena cava (IVC), into the right atrium. Blood moves both passively and actively through the right atrium and tricuspid valve into the right ventricle, which in turn contracts to force blood through the pulmonary valve and into the pulmonary artery. The pulmonary artery directs blood to the lungs, where the blood is oxygenated.

After the blood is oxygenated in the lungs, it returns to the heart through the pulmonary vein and into the left atrium. The left atrium both passively and actively allows blood through the mitral valve and into the left ventricle. The left ventricle then pumps the blood into the aorta, which then distributes the blood to the rest of the body. Blood flow in a patient's body, and particularly the oxygen carried by that person's blood as it courses through their body, is adversely affected by heart failure and lung disease, both of which are pervasive killers.

Heart disease is a significant killer in the U.S., responsible for approximately 1 in 3 deaths (American Heart Association). Approximately 800,000 deaths annually are attributed to heart disease, despite billions in expenditures to fight the disease. When the heart fails to pump an adequate amount of blood, extracorporeal life support (ECLS) can be utilized to bypass the heart and lungs and pump oxygenated blood to the body.

In clinical practice, ECLS (and other practices including extracorporeal membrane oxygenation ("ECMO")) requires a cannula, which is a medical tube inserted into the body for drainage and/or infusion of fluids, such as blood in the case of ECLS. The major problems of available cannulae for ECLS include: (1) cannulation and insertion of cannulae with larger diameters causing extra trauma to patients; (2) the cannula placed in an artery can obstruct distal blood flow due to its large diameter; and (3) damage to adjacent tissue during placement and/or removal.

Thus, currently available arterial cannulae used for cardiopulmonary bypass during surgery and veno-arterial ECLS can obstruct distal flow to the limb in which the cannula is inserted (e.g., the lower leg with femoral cannulation). This can lead to devastating ischemic injury of that limb. Previous efforts to alleviate that risk having included placement of a smaller than desirable sized cannula that will not obstruct the vessel proximally to the point of insertion, or the placement of an additional catheter distally to the point of insertion of the cannula to provide flow to the distal portion of the limb.

Further efforts have been made to provide for distal perfusion, including efforts to provide cannulae with a secondary port positioned proximally to the distal end of the cannula, which secondary port is intended to allow blood to flow into the artery in a direction opposite the flow direction from the distal end of the cannula. For example, U.S. Pat. Nos. 5,171,218 and 5,330,433 to Fonger et al. are directed to an arterial cannula having a diverting side hole positioned proximally on the cannula from the distal end, with barbs on the exterior of the cannula on opposite sides of the diverting side hole. Further, U.S. Pat. No. 8,795,253 and U.S. Patent Application Pub. No. 2014/0330250 to Moshinsky et al. disclose a cannula having a first aperture at a distal end and a second aperture positioned proximally to the distal end, with a protuberance at the second aperture that engages the wall of the patient's blood vessel to prevent its collapse during use. However, such prior efforts have shortcomings, in that they typically exhibit sharp surfaces or facing edges that make it difficult for an operator to place and remove the cannula from the patient's artery, and increase risk of injury to the patient during placement and/or removal. Moreover, such previously known configurations are prone to movement with respect to the patient's artery as the patient moves, risking dislodgement, bleeding, and general injury to the patient.

Accordingly, there remains a need in the art for a device, systems, and methods that will reduce the harm associated with cannulae used during ECLS, that will minimize the risk of blood flow obstruction and damage to the patient's tissue, and that particularly will offer a minimally invasive, efficient, and simple percutaneous cannula for use with ECLS and cardiopulmonary bypass procedures.

SUMMARY OF THE INVENTION

Disclosed herein are devices and methods configured to address one or more of the above described disadvantages of the prior art. However, achieving the above purposes and/or benefits is not a necessary feature to each of the exemplary embodiments, and the claims herein may recite subject matter that does not achieve the above stated purposes.

In accordance with certain aspects of an embodiment of the invention, a bidirectional intravascular cannula, or catheter, is provided that is configured to provide and return blood bidirectionally. For example, the cannula can provide blood to a patient's blood vessel, such as to a patient's arteries, without causing significant blockage that can reduce blood flow to the patient's limbs, even if the cannula is placed proximally in the blood vessel. Thus, the bidirectional intravascular cannula reduces or obviates the need for a second or distal cannula to be placed in a second or opposite direction of flow of currently available unidirectional cannulae. This bidirectional intravascular cannula provides bidirectional flow via a biocompatible reverse flow port. The cannula can be used, by way of non-limiting example, by cardiac surgeons, intensivists, vascular surgeons, ER doctors, IR doctors and cardiologists for peripheral cannulation for ECLS or cardiopulmonary bypass during heart surgery.

In accordance with further aspects of an embodiment of the invention, a bidirectional flow catheter system is provided, comprising: a cannula having a distal end and a proximal end opposite the distal end; a forward flow port at the distal end of the cannula, the forward flow port configured to direct fluid from the cannula in a first direction; a reverse flow port positioned proximally from the distal end of the cannula, the reverse flow port configured to direct fluid from the cannula in a second direction; and a cap positioned on an exterior of the cannula and extending over the reverse flow port.

In accordance with still further aspects of an embodiment of the invention, a bidirectional flow catheter system is provided, comprising: a cannula having a forward flow port at a distal end thereof and a reverse flow port positioned proximally to the distal end; and an obdurator having an outer diameter approximately equal to an interior diameter of the cannula at the distal end of the cannula, the obdurator having a channel in a side wall of the obdurator, the channel having a distal channel end that is proximal to a distal end of the obdurator and a proximal end adjacent to a widened-diameter portion of the cannula; wherein the channel is positioned on the obdurator to align with the reverse flow port when the obdurator is fully inserted into the cannula.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

FIG. 1 is a side view of a bidirectional flow catheter in a blood vessel of a patient in accordance with certain aspects of an embodiment of the invention.

FIG. 1A is a close-up side view of a reverse flow port on the bidirectional flow catheter of FIG. 1.

FIG. 6 is a top view of the reverse flow port on the bidirectional flow catheter of FIG. 1 and showing cross-section lines.

FIG. 6A is a lateral cross-sectional view of the bidirectional flow catheter of FIG. 1 along section line A-A of FIG. 6.

FIG. 6B is a lateral cross-sectional view of the bidirectional flow catheter of FIG. 1 along section line B-B of FIG. 6.

FIG. 6C is a lateral cross-sectional view of the bidirectional flow catheter of FIG. 1 along section line C-C of FIG. 6.

FIG. 7 is a side view of the bidirectional flow catheter of FIG. 1.

FIG. 8 is a top view of the bidirectional flow catheter of FIG. 1.

DETAILED DESCRIPTION OF THE PREFERRED EMBODIMENTS

Figure 2:
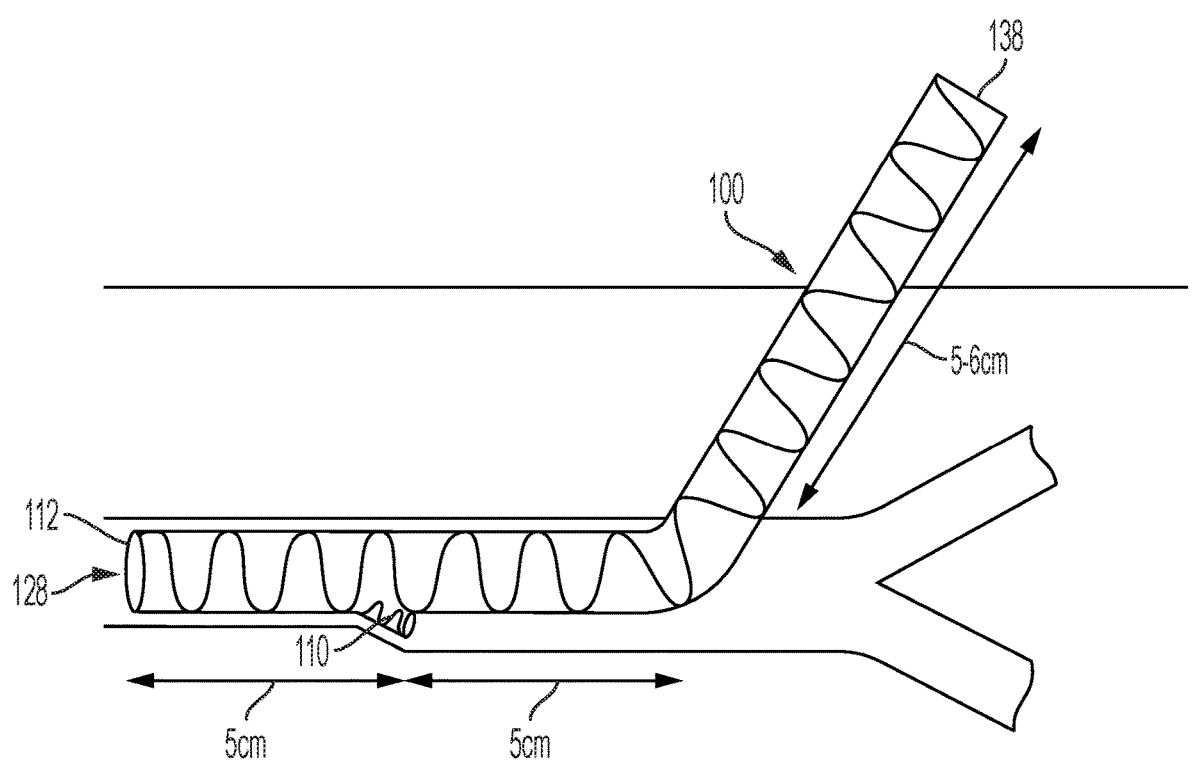
FIG. 2 is a side view of the bidirectional flow catheter of FIG. 1 in a common femoral artery.

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art. Descriptions of well-known functions and structures are omitted to enhance clarity and conciseness.

Hereinafter, an apparatus and method for enabling bidirectional flow during extracorporeal life support (ECLS) or cardiopulmonary bypass is disclosed. Embodiments of the invention may, however, be configured in many different forms for various other procedures and should not be construed as limited to the exemplary embodiments set forth herein. Rather, these exemplary embodiments are provided so that this disclosure is thorough, and will fully convey the scope of the invention to those skilled in the art.

Throughout the drawings and the detailed description, unless otherwise described, the same drawing reference numerals are understood to refer to the same elements, features, and structures. The relative size and depiction of these elements may be exaggerated for clarity.

It will be understood that for the purposes of this disclosure, "at least one of X, Y, and Z" can be construed as X only, Y only, Z only, or any combination of two or more items X, Y, and Z (e.g., XYZ, XZ, XYY, YZ, ZZ). Further, it will be understood that when an element is referred to as being "connected to" another element, it can be directly connected to the other element, or intervening elements may be present.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

Referring to FIGS. 1-21, a bidirectional intravascular cannula 100 or catheter is provided, which in certain configurations may be used in peripheral ECLS, such as extracorporeal membrane oxygenation (ECMO) or cardiopulmonary bypass to provide and return blood bidirectionally to a patient's blood vessel. In an exemplary embodiment, the cannula 100 is a single cannula that is configured to provide bidirectional blood flow using a reverse flow port 110. For example, the cannula 100 can be inserted into a patient's blood vessel to provide blood in a first direction from a distal end 124 of the cannula 100, such as toward the patient's heart, and in a second direction (preferably opposite to the first direction) from a reverse flow port 110, such as to flow toward the distal portion of the patient's limb in which cannula 100 has been placed. Thus, the bidirectional intravascular cannula 100 reduces or obviates the need for a second cannula, such as a currently available unidirectional cannula used in veno-arterial ECLS procedures, to be placed in a second or opposite direction of flow. As discussed below, the cannula 100 is further configured to be inserted into the patient at an insertion location while reducing damage to tissue adjacent to the insertion location, compared to typical cannula. The cannula 100 is still further configured to remain stably positioned in the patient at the insertion location of the patient when perturbed, such as when the patient moves or when a line coupled to the cannula 100 is perturbed. This bidirectional intravascular cannula 100 provides bidirectional blood flow via reverse flow port 110 and forward flow port 112 at the distal end 124 of cannula 100, as further discussed below, which are biocompatible.

With particular reference to FIGS. 1, 2, 5, 7 and 8, cannula 100 according to certain aspects of an embodiment includes a cannula lumen 114 extending through cannula 100 from a proximal end 122 to a distal end 124 of cannula 100, a forward flow port 112 at distal end 124 of cannula 100, a reverse flow port 110 positioned proximally from distal end 124 of cannula 100 and extending through a sidewall of cannula 100 from an exterior of cannula 100 into lumen 114, a cap 116 on the exterior wall of cannula 100 extending over most or all of reverse flow port 110, and a coupling 118 adjacent the proximal end 122 of cannula 100. The lumen 114 of cannula 100 is a generally arcuate lumen having a proximal end that coincides with the proximal end 122 of cannula 100, and a distal end that coincides with distal end 124 of cannula 100, and is configured to fluidly and percutaneously communicate blood from an inlet portion 126 of cannula 100 to an outlet portion 128 of cannula 100. For example, in one embodiment the inlet portion 126 is integrally formed with coupling 118 at the proximal end 122 of cannula 100, and the outlet portion 128 includes the reverse flow port 110 and the forward flow port 112 near the distal end 124 of the cannula 100. Coupling 118 is configured to couple and operate with typical ECLS tubing and equipment (not shown). The cannula lumen 114 of the current embodiment can be various diameters, similar to typical cannulas, such as 12-25 French, although other diameters may be employed for particular situations as desired by an operator without departing from the spirit and scope of the invention.

In a particular embodiment, the general arcuate cannula lumen 114 does not have a particularly fixed angle between the proximal end 122 and distal end 124 of cannula 100. For example, the general arcuate cannula lumen 114 can have an angle between the proximal end 122 and distal end 124 of approximately 15 degrees, or between 5 degrees and 180 degrees.

Cannula 100 is preferably formed of a biocompatible material, such as a metal (e.g., alloy, stainless steel, titanium, etc.), plastic (e.g., PEEK, PMMA, Nylon, Polyurethane, etc.), ceramic, composite, or the like. In an exemplary embodiment, cannula 100 is formed as one piece of material; however, cannula 100 may alternatively be formed of multiple pieces of material (e.g., the cannula 100 is formed as one component and the coupling 118 and/or cap 116 are formed as another component that are attached to the cannula 100 component). Furthermore, cannula 100 can be formed according to many typical manufacturing methods, such as dipping, machining, injection molding, lay-ups, additive manufacturing methods, and the like. Still further, cannula 100 may include a biocompatible coating (such as polyethylene or the like) to protect cannula 100, reduce friction, or improve flow. In certain configurations, cannula 100 may include structural reinforcement to increase the strength and rigidity of the cannula 100, as shown in FIG. 2. By way of non-limiting example, such structural reinforcement may comprise a thin reinforcement wire 138, which is generally covered by a coating (such as the biocompatible coating discussed above) to provide a smooth surface.

Figure 4:
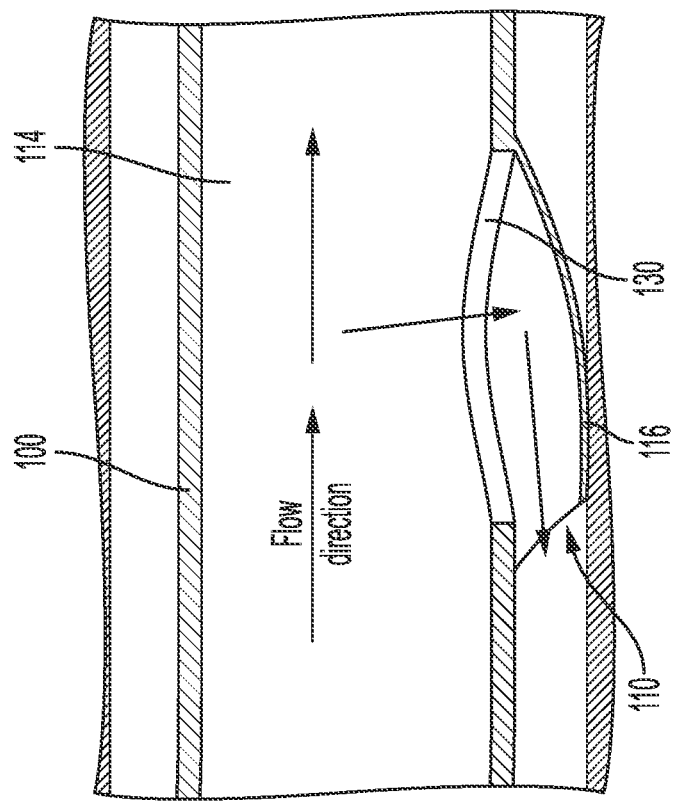
FIG. 4 is a close-up, cross-section view of a reverse flow port on the bidirectional flow catheter of FIG. 1 and showing a blood flow direction.
Figure 3:
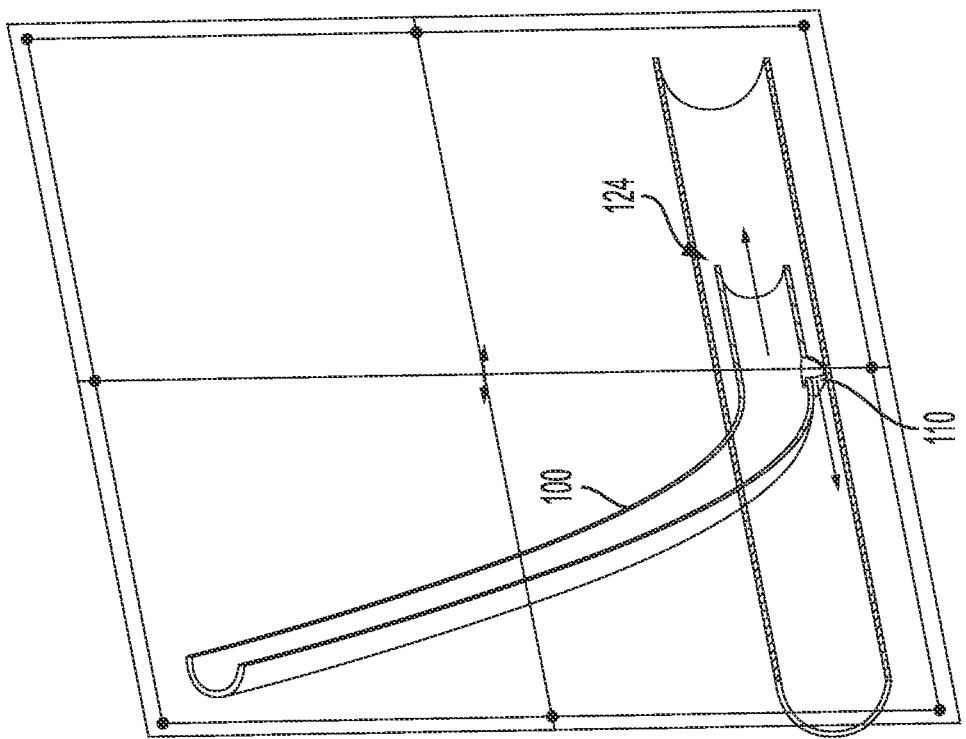
FIG. 3 is a cross-sectional view of the bidirectional flow catheter of FIG. 1 in a blood vessel and showing a blood flow direction.
Figure 9:
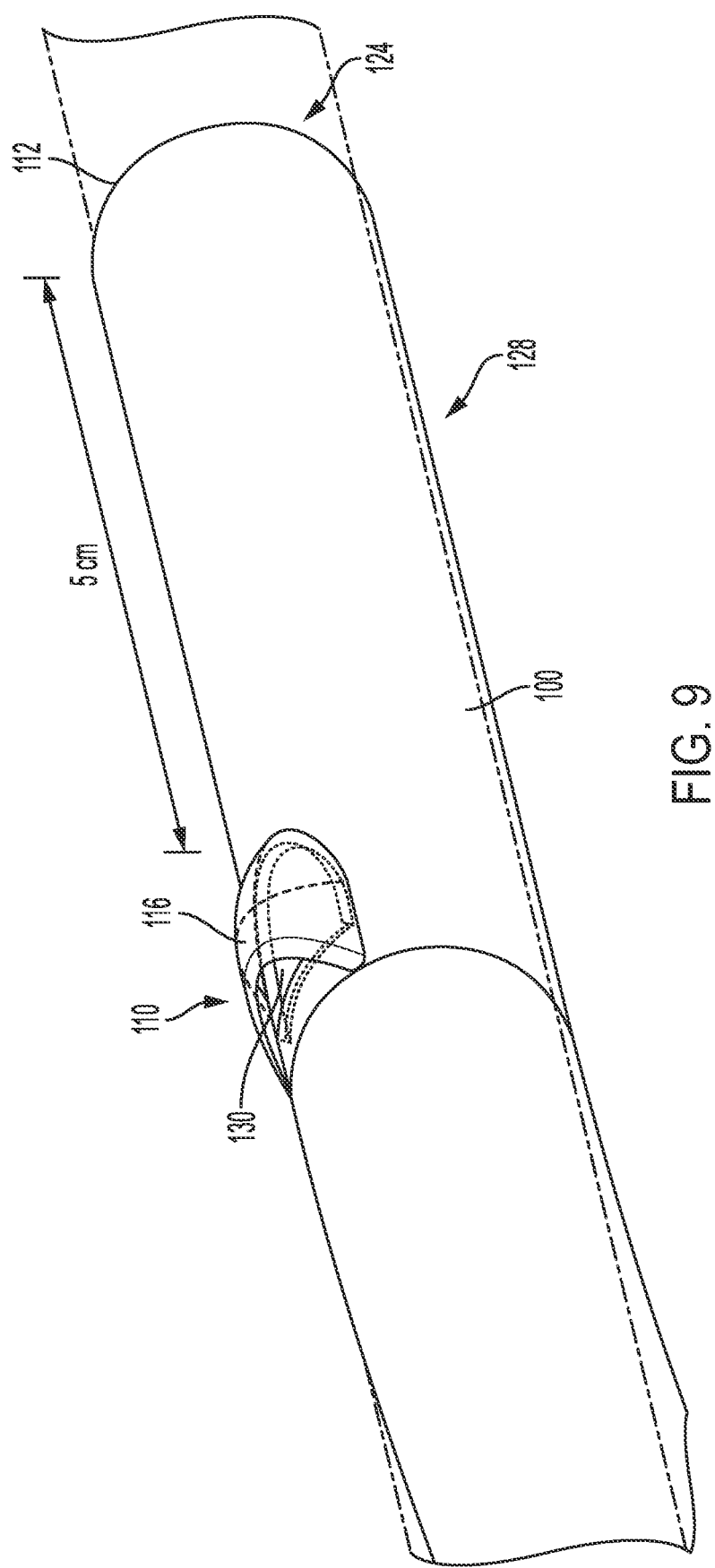
FIG. 9 is a close-up perspective view of the reverse flow port on the bidirectional flow catheter of FIG. 1.
Figure 10A:
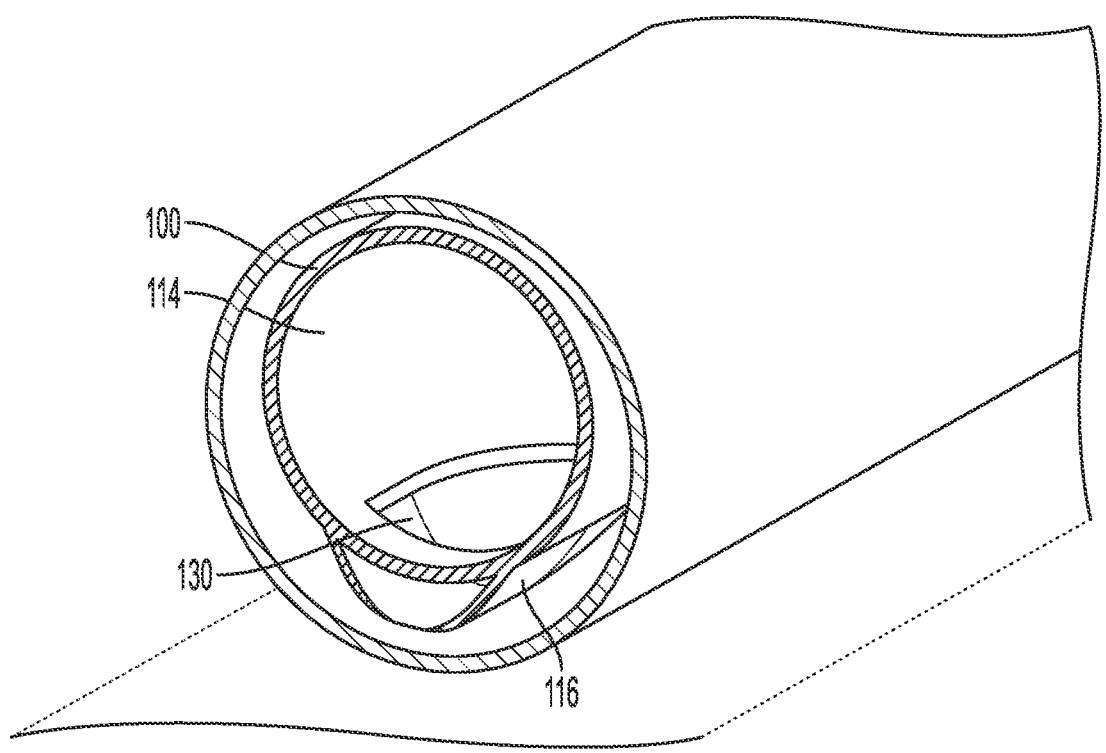
FIG. 10A is a close-up, side perspective cross-sectional view of the bidirectional flow catheter of FIG. 1 in a blood vessel at the location of the reverse flow port.
Figure 10B:
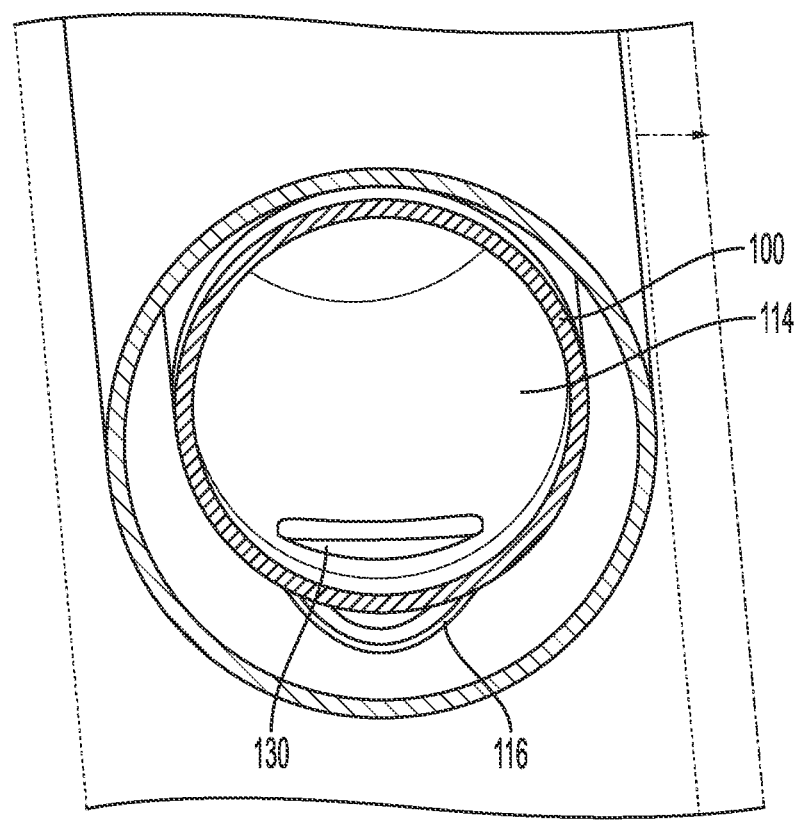
FIG. 10B. is close-up, front perspective cross-sectional view of the bidirectional flow catheter of FIG. 1 in a blood vessel at the location of the reverse flow port.
Figure 11:
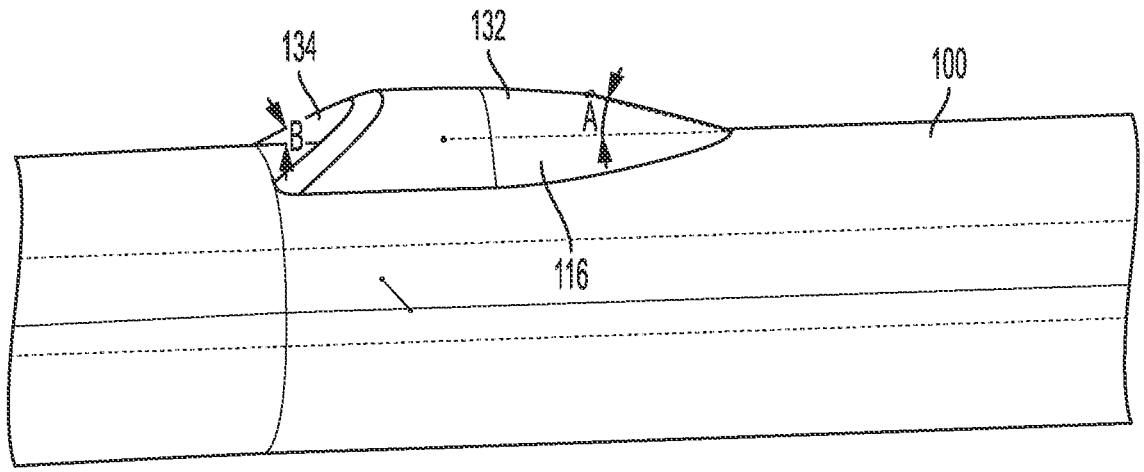
FIG. 11 is a close-up, side view of the bidirectional flow catheter of FIG. 1 showing exemplary dimensions of portions of the reverse flow port.
Figure 12:
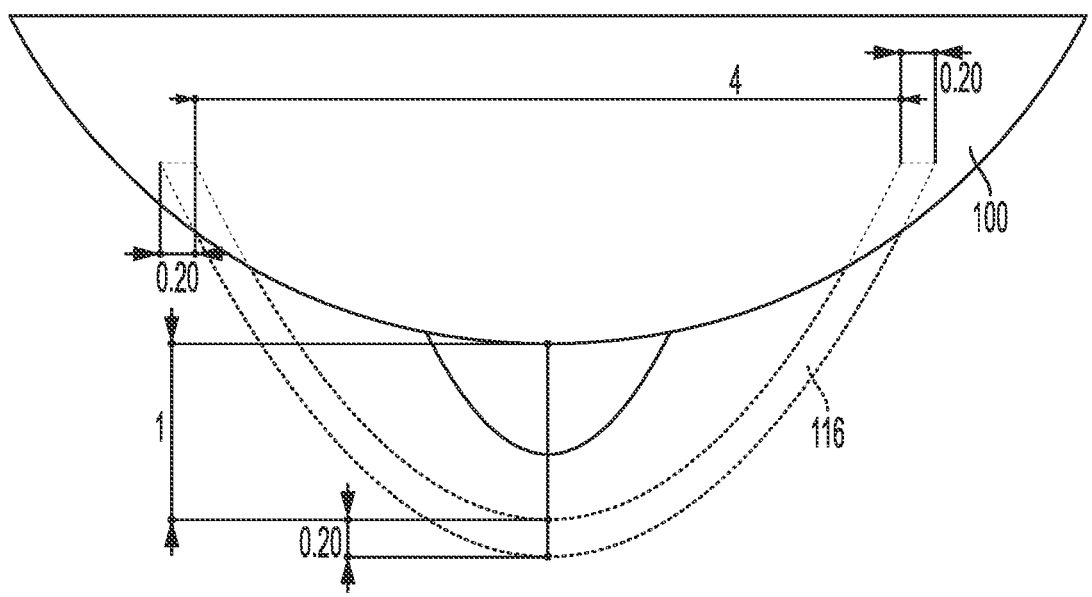
FIG. 12 is a close-up, front view of the reverse flow port on the bidirectional flow catheter of FIG. 1 showing exemplary dimensions of portions of the reverse flow port.
Figure 13:
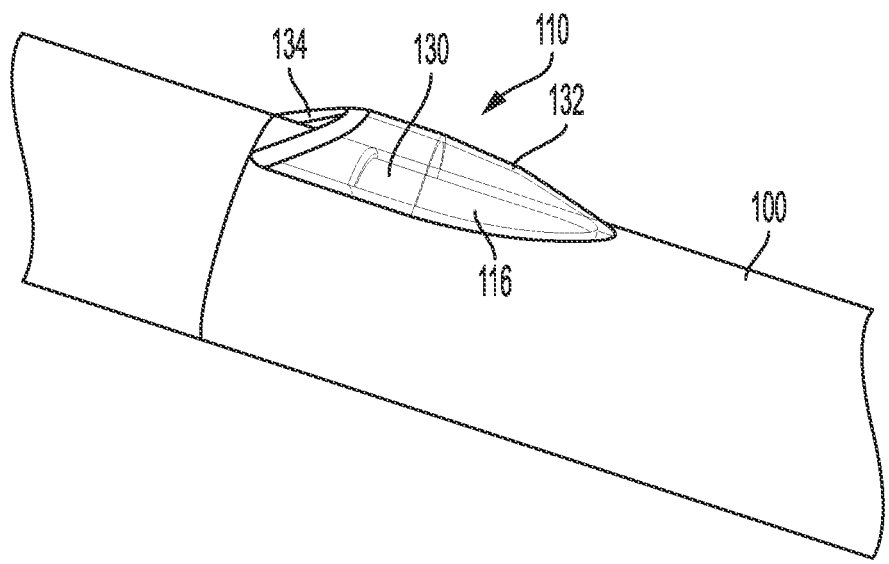
FIG. 13 is a close-up, side perspective view of the bidirectional flow catheter of FIG. 1 with a cap over the aperture of the reverse flow port shown in phantom.

Next, and with reference to FIGS. 1, 3, and 4, reverse flow port 110 is configured to provide blood flow in a different and preferably reverse direction relative to blood flow within the cannula lumen 114 and from the forward flow port 112. For example, FIGS. 3 and 4 show the cannula 100 providing for blood flowing through the cannula lumen 114 from the proximal end 122 of cannula 100 to the forward flow port 112, and the reverse flow port 110 configured to provide blood flow from the cannula lumen 114 into the blood vessel away from the forward flow port 112 (i.e., away from the distal end 124 of cannula 100). In a particularly preferred embodiment, and as shown in FIG. 9, a distal end of reverse flow port 110 is positioned 5 cm from the distal end 124 of cannula 100 so as to ensure adequate flow in both directions without excessive turbulence or other interference between the flows. As discussed in greater detail below, the outer surface of cap 116 over reverse flow port 110 is further configured to reduce damage (e.g., compared to a typical ECLS cannula) to the patient's tissue (e.g., skin, muscle, and blood vessels) when placing, inserting, or removing the cannula 100. In an embodiment, cannula 100 is placed into a patient's blood vessel according to typical methods and guidelines. Also as discussed in greater detail below, cap 116 over reverse flow port 110 is still further configured to reduce the likelihood that the cannula 100 will inadvertently displace from the patient, for example, when cannula 100 is perturbed or the patient moves, and also reduce damage to the patient's tissue if cannula 100 is perturbed or inadvertently displaced from the patient, compared to a typical cannula.

In an embodiment, reverse flow port 110 includes an aperture 130 or hole (see FIGS. 4, 5, 9, 13, 14, and 17-19) extending through the wall of cannula 100 from lumen 114 to the exterior of cannula 100. The aperture 130 is configured to fluidly communicate blood flow from the cannula lumen 114 to the patient's blood vessel. More particularly, a portion of blood flowing through lumen 114 toward distal end 124 of cannula 100 will escape through aperture 130 before it reaches distal end 124 of cannula 100. The interior of cap 116 is configured to generally direct blood flow that escapes from lumen 114 through aperture 130 in a desired direction, such as a direction opposite to the direction of blood flow from the forward flow port 112, while the exterior of cap 116 is configured to reduce the likelihood of damage to the patient's tissue, as described herein. The combination of the cap 116 configured as described herein and aperture 130 fluidly communicate blood flow from the cannula lumen 114 to the patient's blood vessel, as described above, while providing preferential blood flow properties, such as desired blood flow velocity and reducing turbulence. Furthermore, in a particular embodiment and as discussed above, the reverse flow port 110 and the forward flow port 112 are spaced relative to each other along the cannula lumen 114, such as by a distance of 5 cm, to reduce the likelihood of damage, etc., as described above (see, e.g., FIG. 2). For example, the reverse flow port 110 can be displaced approximately 5 cm from the forward flow port 112. The reverse flow port 110 can be displaced approximately 5 cm forward of the insertion point of the cannula 100 into the patient's blood vessel. As a further example, the reverse flow port 110 is displaced distal of an arcuate portion of the cannula 100, such as positioned on a straight portion of the cannula 100.

With continuing reference to FIGS. 1A, 4-6, and 9-16, and in accordance with certain aspects of an embodiment, cap 116 is on the exterior of cannula 100 and generally covers aperture 130. The exterior of cap 116 generally has a convex, parabolic, and ramp-like shape, such that the cap 116 fluidly communicates blood flow in one direction only. However, in alternative embodiments, the cap 116 can be configured to communicate blood flow in a plurality of directions. As shown in the top views of cap 116 of FIGS. 5 and 6, and in accordance with certain aspects of an embodiment, cap 116 generally has a parabola-like outline, such that it is formed by a body portion 132 that has a ramp-like shape that intersects a bottom portion 120 of the exterior of cannula 100, and a leg portion 134 (e.g., having two leg-like shapes 134a and 134b) that generally intersects with side portions 136 of the exterior of cannula 100 (see FIGS. 5, 6, 6B, and 6C). Body portion 132 of cap 116 is generally convex to direct blood flow in a desired direction while reducing the likelihood of inducing turbulence. In an embodiment, the exterior of the body portion 132 of the cap 116 is generally configured to rest on an inner wall of a patient's blood vessel, such that the inner wall of the blood vessel does not substantially interfere with blood flow between aperture 130 and the blood vessel. As best seen in FIG. 1A, the exterior surface of cap 116 is configured to contact and displace the inner wall of the blood vessel so as to optimally position aperture 130 with respect to the inner wall of the blood vessel. In a particular embodiment, in order to achieve such optimal positioning of aperture 130 with respect to the inner wall of the patient's blood vessel to provide optimal flow characteristics, and with reference to FIG. 12, cap 116 may have a height (from the exterior of cannula 100 to the interior face of cap 116) of, for example, between 0.5 mm and 3 mm, and more preferably between 0.8 mm and 2 mm, and most preferably 1 mm, with the wall of cap 116 having a thickness of preferably between 0.05 mm and 2 mm, and more preferably of 0.2 mm, and a maximum width at a proximal end of cap 116 of preferably 4 mm. Furthermore, the rounded nature of the body portion 132 and leg portion 134 provides cap 116 a shape that is configured to slide on the patient's tissue without entangling or snaring the patient's tissue to reduce the likelihood of damage to the patient's tissue when placing the cannula 100 in the patient and when removing the cannula 100 from the patient (e.g., desired or inadvertent), as described above, such that cap 116 has no substantially sharp, abrupt, or barb-like surfaces.

Further, body portion 132 and leg portion 134 of cap 116, in accordance with further aspects of an embodiment, are configured to achieve the desired flow properties. The body portion 132 generally forms the parabola-like outline of the cap 116, and extends from the cannula lumen 114 to the leg portion 134 at a ramp angle. The ramp angle ("A" of FIG. 11) of body portion 132 of cap 116 reduces the likelihood of damage to the patient's tissue during insertion by providing a substantially smooth surface, as discussed above. Likewise, the ramp angle ("B" of FIG. 11) of leg portion 134 of cap 116 reduces the likelihood of damage to the patient's tissue during removal, with both body portion 132 and leg portion 134 having no substantially sharp, abrupt, or barb-like surfaces. In a particular embodiment, the ramp angle A of body portion 132 is preferably in the range of 10 degrees to 70 degrees, and more preferably in the range of 15 degrees to 22 degrees. Likewise in a particular embodiment, the ramp angle B of leg portion is preferably in the range of 10 degrees to 70 degrees, and more preferably 20 degrees. Leg portion 134 includes two elongated leg-like features 134a and 134b that each extend from the body portion 132 on the bottom portion 120 of cannula 100 to the side portions 136 of cannula 100. Thus, cap 116 is particularly configured to reduce the likelihood of cross-flow (e.g., blood flow in the blood vessel between the reverse flow port 110 and the forward flow port 112) by reducing the likelihood of blood flow around the leg portion 134. The leg portion 134 is generally angled from the side portions 136 of the cannula lumen 114 to the body portion 132, such that the leg portion 134 generally has an arcuate and concave outline (best viewed in FIG. 1A). The angle of the leg portion 134 may vary according to various properties of the cannula 100, such as the cannula lumen diameter, the desired blood flow properties (e.g., direction, velocity, turbulence), and placement location. Furthermore, the angle of the leg portion 134 and concave outline may be selected to reduce the likelihood of damage to the patient's tissue by providing a smooth surface, as discussed above, such as having no substantially sharp, abrupt, or barb-like surfaces. In an alternative embodiment, the leg-like features 134a and 134b may have unequal angles and/or arcuate shapes.

Figure 5:
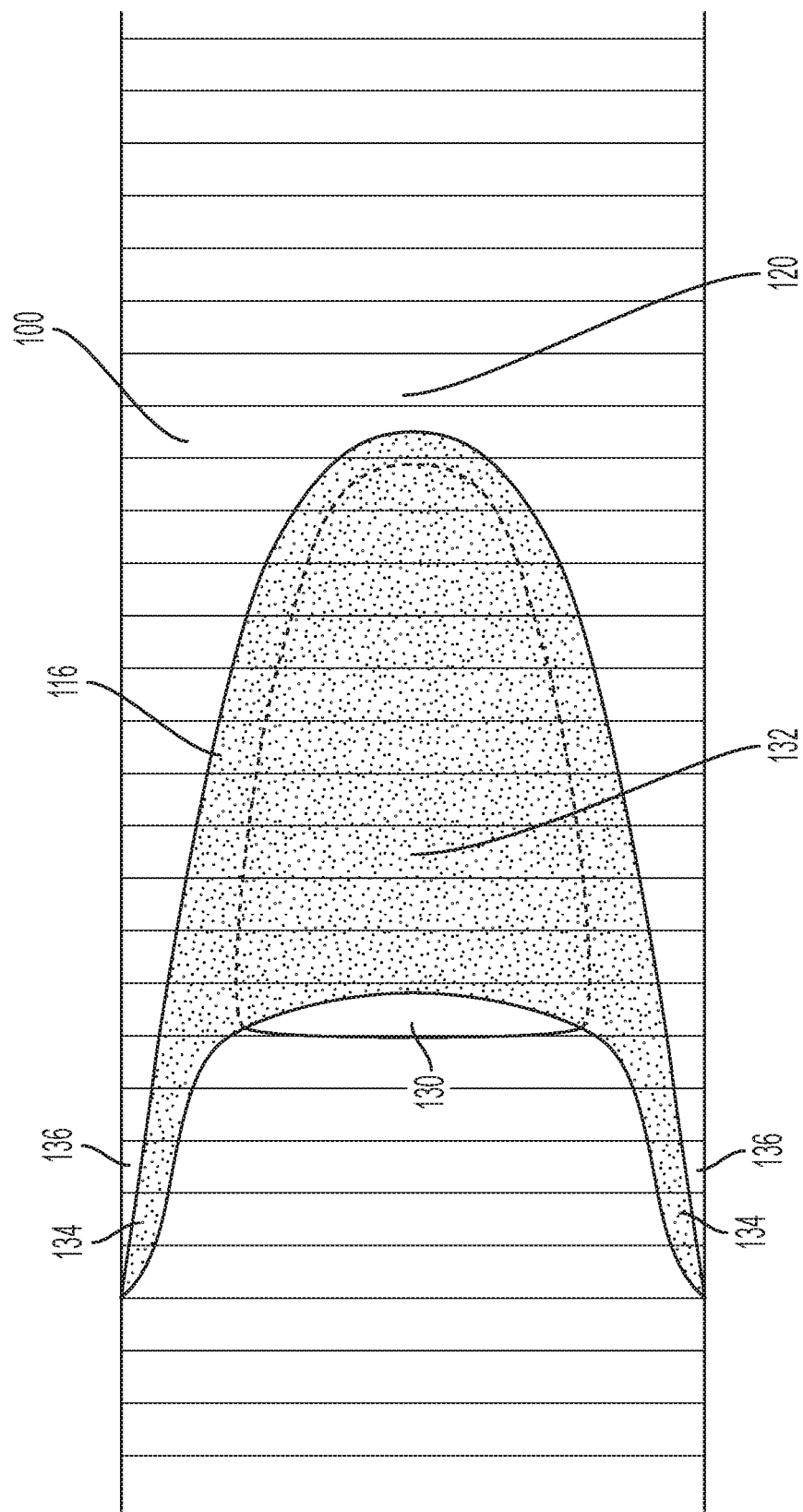
FIG. 5 is a top view of the reverse flow port on the bidirectional flow catheter of FIG. 1.
Figure 14:
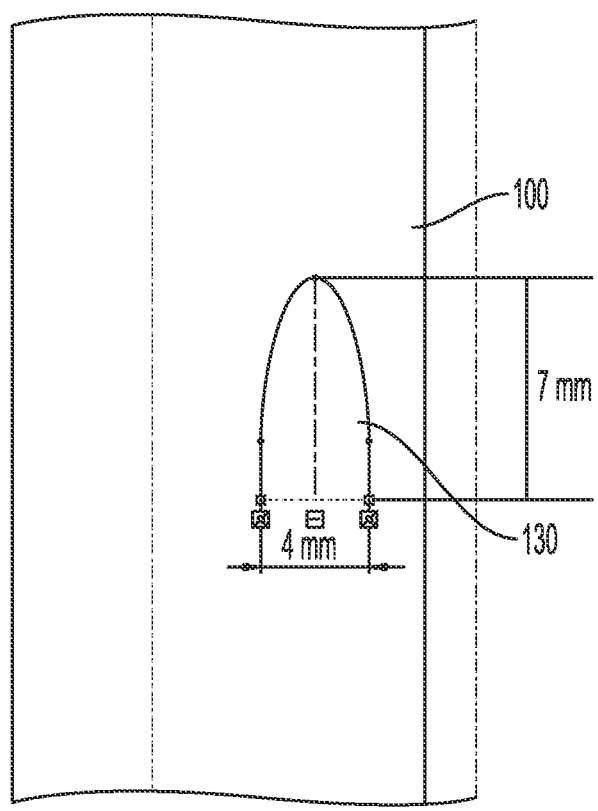
FIG. 14 is a close-up, top view of the aperture of the reverse flow port showing exemplary dimensions of the aperture.
Figure 15:
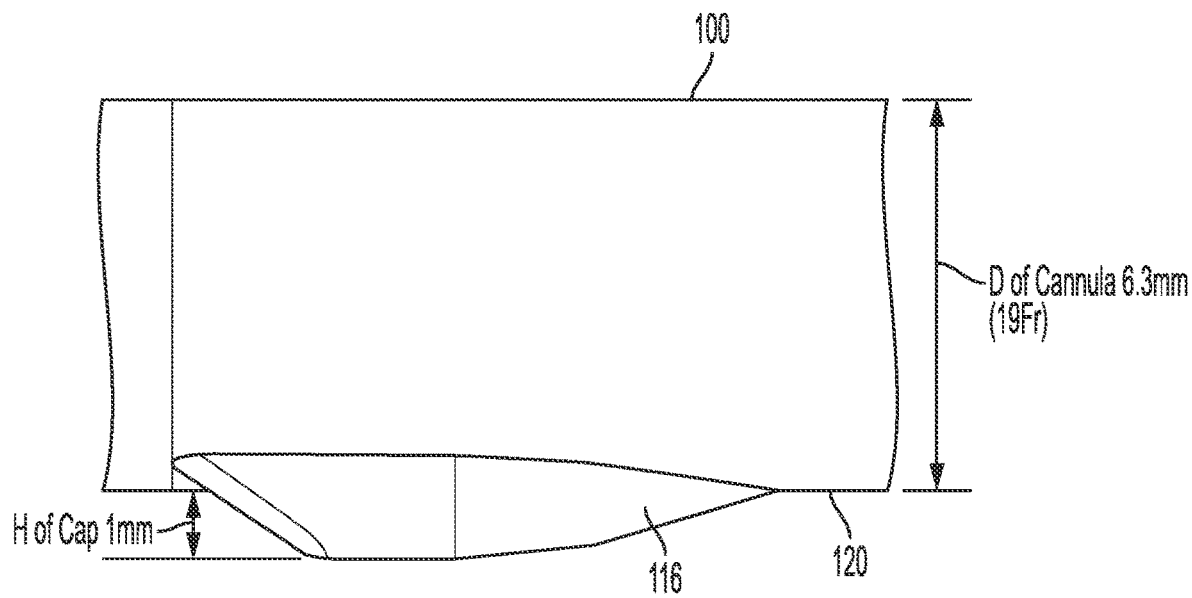
FIG. 15 is a close-up, side view of the cap of the reverse flow port showing exemplary dimensions of the cap.
Figure 16:
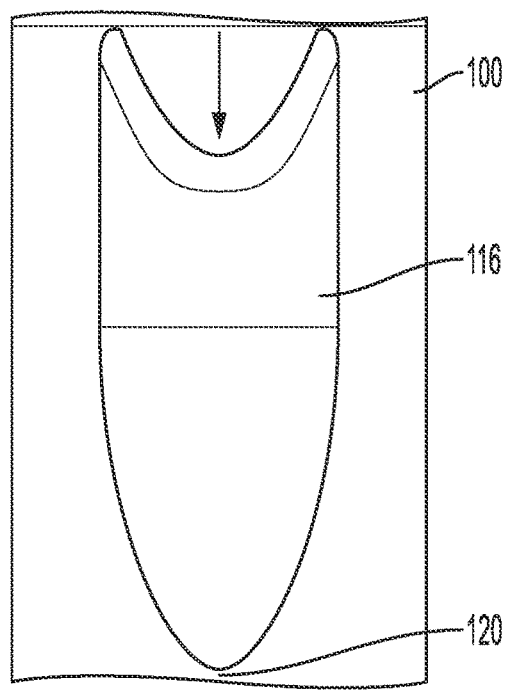
FIG. 16 is a close-up, top view of the cap of the reverse flow port.
Figure 17:
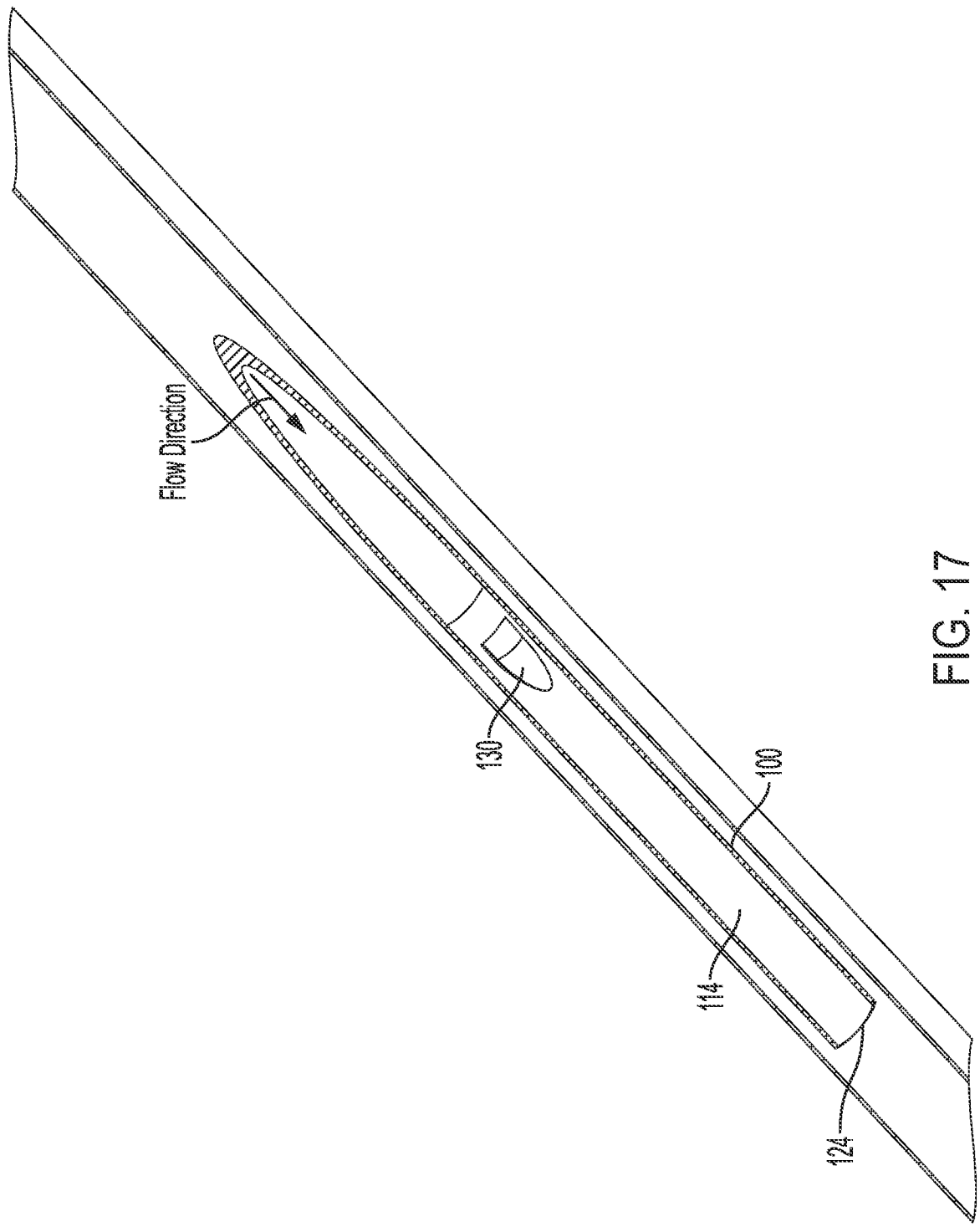
FIG. 17 is a top, side perspective, horizontal cross-sectional view of the bidirectional flow catheter of FIG. 1 and showing a flow direction.
Figure 18:
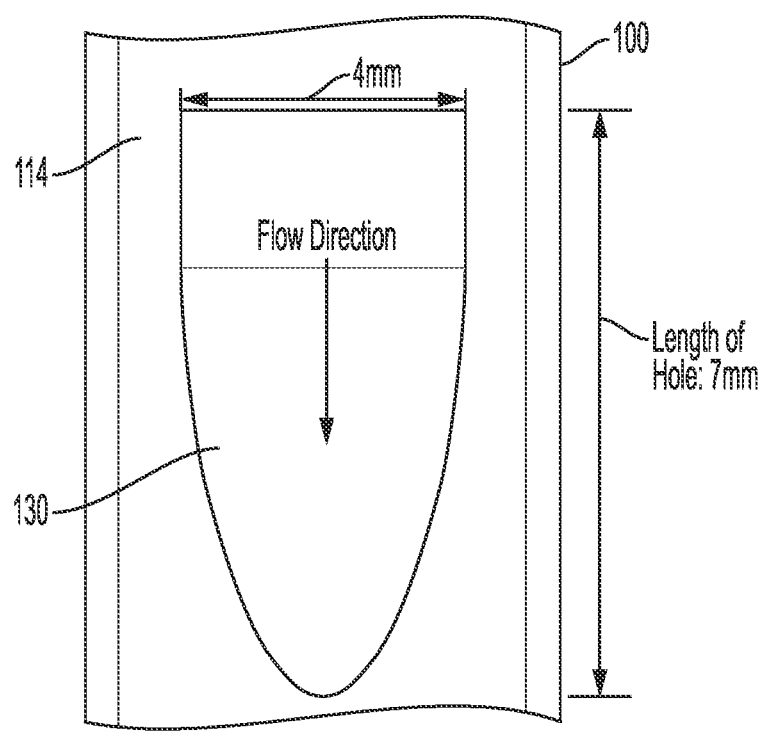
FIG. 18 is a close-up, top horizontal cross-sectional view of the bidirectional flow catheter of FIG. 1 showing a flow direction from the lumen of the cannula into the reverse flow port.
Figure 19:
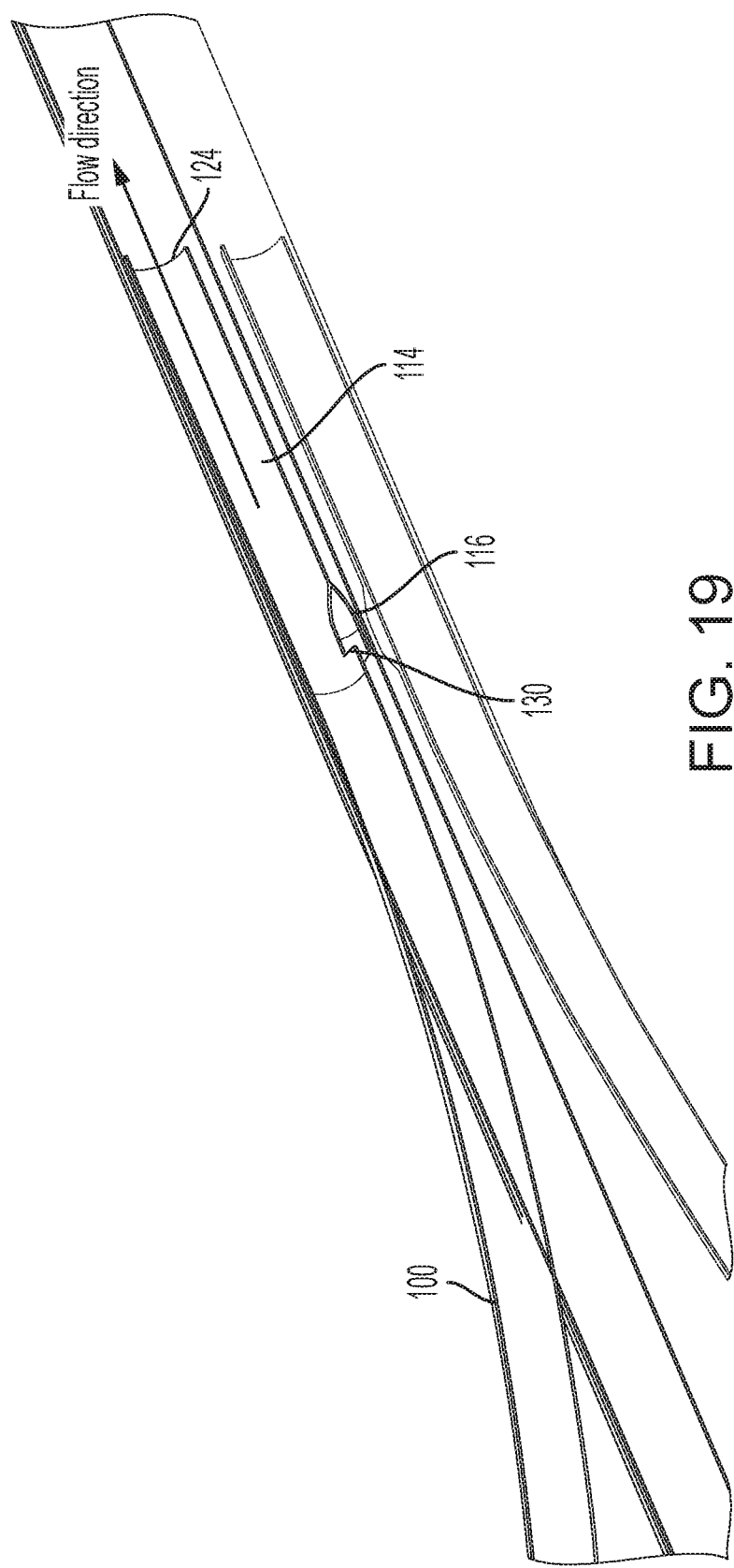
FIG. 19 is a top, side perspective, vertical cross-sectional view of the bidirectional flow catheter of FIG. 1 and showing a flow direction.

Aperture 130 is configured to fluidly communicate blood flow from the cannula lumen 114 to the patient's blood vessel. In a particular embodiment, aperture 130 of the current embodiment has a parabola-like opening similar to the parabola-like outline of the cap 116, as shown in FIGS. 5 and 14, in which the vertex of the parabola is located at the distal-most portion of aperture 130 (closest to forward flow port 112). However, aperture 130 may have a different opening size or shape compared to the cap 116. In a particular embodiment, aperture 130 has an opening size that is generally similar to the diameter of the cannula lumen 114, such as 12-23 French. For example, FIG. 5 shows a top view of cap 116 (shaded) and aperture 130 (dashed line) that do not strictly overlap, but have a generally similar outline. In a particular embodiment and as shown in FIG. 18, the aperture 130 has an opening that is approximately 4 mm wide and approximately 7 mm long. Alternatively, aperture 130 may have an ellipsoidal-like opening as shown in FIG. 4.

Now referring to FIGS. 1-3, 7-9, and 19, forward flow port 112 is configured to fluidly communicate blood from the cannula lumen 114 into the patient's blood vessel in a proximal direction (e.g., towards the heart and other arteries). In accordance with a particular embodiment, forward flow port 112 has a cross-sectional opening that is similar to the cross-section of cannula 100, while reverse flow port 110 is configured to communicate blood flow from the cannula lumen 114 into the blood vessel away from the forward flow port 112 (e.g., away from the distal end 124 of cannula 100). In other configurations, forward flow port 112 may include a plurality of apertures or fenestrations.

Coupling 118 adjacent proximal end 122 of cannula 100 may be configured to attach to standard medical equipment, such as ECLS devices or any device for circulating blood through a major blood vessel having blood flow in an opposing direction, such as cardiac bypass, mechanical arterial support, venous access device (VAD) support, or the like.

Figure 20:
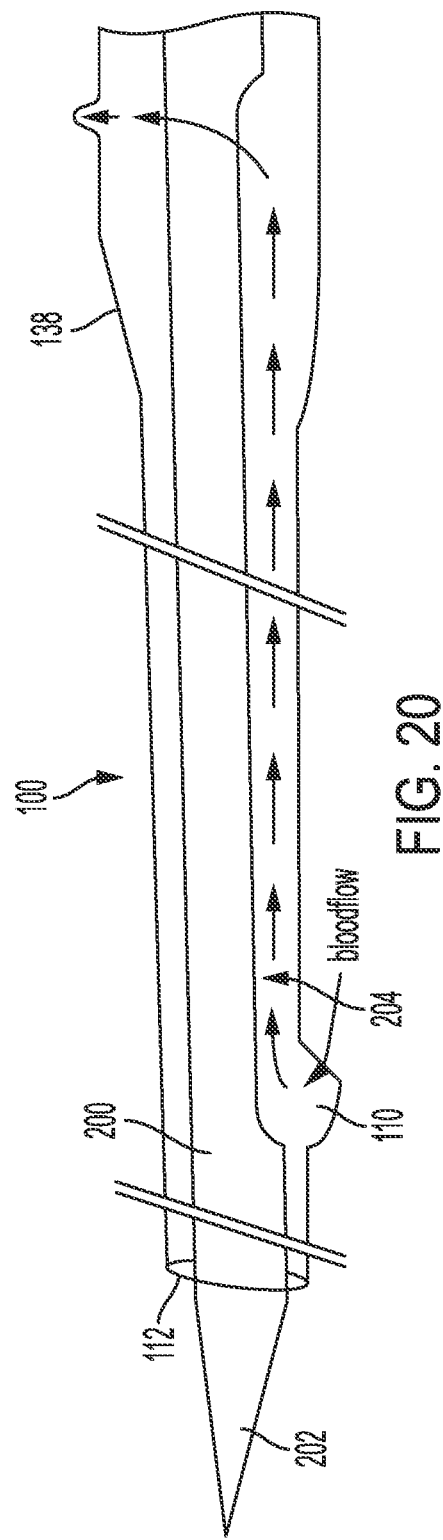
FIG. 20 is a side view of the bidirectional flow catheter of FIG. 1 with an obdurator full inserted into the catheter.
Figure 21:
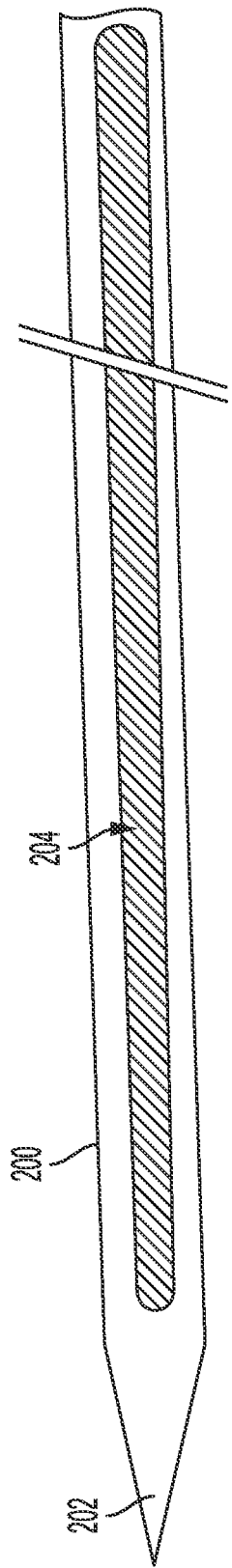
FIG. 21 is a bottom view of the obdurator of FIG. 20.

Next, and with reference to FIGS. 20 and 21, an obdurator 200 may be provided for use with cannula 100 for placement of cannula 100 within a patient's blood vessel. Obdurator 200 is a solid member having an outside diameter approximately the same as the inside diameter of cannula lumen 114 at the distal end 124 of cannula 100, and is sufficiently long so that the distal end 202 of obdurator 200, when inserted in cannula 100, extends beyond the distal end 124 of cannula 100. In use, access may be gained to the vessel (such as by making an incision) and the obdurator 200 is inserted into cannula 100, with distal end 202 of obdurator 200 extending beyond the distal end 124 of cannula 100. Obdurator 200 then pushes through the patient's soft tissue and into the patient's blood vessel, gaining entrance for cannula 200. Once inserted in place, obdurator 200 is removed, leaving cannula 100 in place in the patient's blood vessel.

Obdurator 200 is particularly configured to enable an operator to know when reverse flow port 110 is positioned within the patient's blood vessel. More particularly, obdurator 200 includes a concave channel 204 extending into the surface of obdurator 200. Concave channel has a distal end closest to distal end 124 of lumen 114 that, when obdurator 200 is fully inserted into cannula 100, aligns with or is distal to reverse flow port 110 (as show in FIG. 20). Channel 204 allows blood to flow in cannula 100 when obdurator 200 is in place within cannula 100, with such blood flowing from the patient's blood vessel into reverse flow port 110, into channel 204, and proximally through channel 204 (toward the proximal end 122 of cannula 100) into a widened section 138 of cannula 100 and ultimately toward preferably a luer locked hole (not shown) positioned near proximal end of cannula 100, such as on coupling 118. With obdurator 200 completely inserted into cannula 100, the distal end of concave channel 204 aligns with reverse flow port 110. As reverse flow port 110 enters the patient's blood vessel, arterial pressure will push blood through reverse flow port 110, into concave channel 204 in obdurator 200, and fill the empty lumen 114 of cannula 100 to finally exit out of the luer locked hole near the proximal end 122 of cannula 100. In a particular configuration, concave channel 204 has a depth into the surface of obdurator 200 and a width that is 5-30% of the diameter of obdurator 200.

Disclosed above is a bidirectional intravascular cannula, or catheter, that is configured to provide and return blood bidirectionally. The bidirectional intravascular cannula reduces or obviates the need for a second cannula to be placed in a second or opposite direction of flow of currently available unidirectional cannulae. The cannula is further configured to be inserted into the patient at an insertion location while reducing damage to tissue, compared to typical cannula, which is adjacent to that insertion location. This bidirectional intravascular cannula provides bidirectional flow via a biocompatible, reverse flow port. The cannula is further configured to stably remain in the patient at the insertion location of the patient when perturbed, such as when the patient moves slightly or when a line coupled to the cannula is perturbed. This bidirectional intravascular cannula provides bidirectional flow via a reverse flow port and the forward flow port, which are biocompatible.

While the exemplary embodiments have been shown and described, it will be understood by those skilled in the art that various changes in form and details may be made thereto without departing from the spirit and scope of the present disclosure as defined by the appended claims.

In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. A bidirectional flow catheter system, comprising:
a cannula having a distal end and a proximal end opposite said distal end;
a forward flow port at said distal end of the cannula, said forward flow port configured to direct fluid from said cannula in a first direction;
a reverse flow port positioned proximally from said distal end of said cannula, said reverse flow port configured to direct fluid from said cannula in a second direction; and
a cap positioned on an exterior of said cannula and extending over said reverse flow port, wherein said cap has a convex exterior surface facing away from an outer wall of the cannula, said cap having a distal portion closest to the distal end of the cannula that fully covers the reverse flow port, and a proximal portion having a pair of proximally extending legs positioned outward from side edges of the reverse flow port.

2. The bidirectional flow catheter system of claim 1, wherein said cap has a concave interior surface facing the outer wall of the cannula.

3. The bidirectional flow catheter system of claim 2, wherein said concave interior surface is configured to direct fluid passing from a lumen within the cannula and through the reverse flow port in said second direction.

4. The bidirectional flow catheter system of claim 3, wherein said second direction is opposite said first direction.

5. The bidirectional flow catheter system of claim 1, wherein said reverse flow port defines an elliptical curve having a vertex at a distal-most edge of the reverse flow port.

6. The bidirectional flow catheter system of claim 1, wherein said reverse flow port extends through a sidewall of the cannula to provide fluid communication between a patient's blood vessel and a lumen extending through the cannula.

7. The bidirectional flow catheter system of claim 1, further comprising an obdurator having an outer diameter approximately equal to an interior diameter of the cannula at the distal end of the cannula so as to occlude fluid flow through the distal end of the cannula, said obdurator having a channel in a side wall of the obdurator, said channel having a distal channel end that is proximal to a distal end of the obdurator and a proximal end adjacent to a widened-diameter portion of the cannula.

8. The bidirectional flow catheter system of claim 7, wherein said channel is positioned on said obdurator to align with said reverse flow port when the obdurator is fully inserted into the cannula.

9. The bidirectional flow catheter system of claim 7, said cannula further comprising a luer lock in fluid communication with said channel.

10. A bidirectional flow catheter system, comprising:
  a cannula having a forward flow port at a distal end thereof and a reverse flow port positioned proximally to said distal end; and
  an obdurator having an outer diameter approximately equal to an interior diameter of the cannula at the distal end of the cannula, said obdurator having a channel in a side wall of the obdurator, said channel having a distal channel end that is proximal to a distal end of the obdurator and a proximal end adjacent to a widened-diameter portion of the cannula;

wherein said channel is positioned on said obdurator to align with said reverse flow port when the obdurator is fully inserted into the cannula.

11. The bidirectional flow catheter system of claim 10, said cannula further comprise a cap positioned on an exterior of said cannula and extending over said reverse flow port.

12. The bidirectional flow catheter system of claim 11, wherein said cap has a concave interior surface facing an outer wall of the cannula.

13. The bidirectional flow catheter system of claim 12, wherein said concave interior surface is configured to direct fluid passing from a lumen within the cannula and through the reverse flow port in a first direction different from a second direction of fluid passing out of the distal end of the cannula.

14. The bidirectional flow catheter system of claim 13, wherein said first direction is opposite said second direction.

15. The bidirectional flow catheter system of claim 10, wherein said cap has a convex exterior surface facing away from an outer wall of the cannula.

16. The bidirectional flow catheter system of claim 15, said cap having a distal portion closest to the distal end of the cannula that fully covers the reverse flow port, and a proximal portion having a pair of proximally extending legs positioned outward from side edges of the reverse flow port.

* * * * *